(12) United States Patent
Accisano, III

(10) Patent No.: US 11,413,437 B2
(45) Date of Patent: Aug. 16, 2022

(54) EXPANDABLE INTRODUCER ASSEMBLY

(71) Applicant: Merit Medical Systems, Inc., South Jordan, UT (US)

(72) Inventor: Nicholas Accisano, III, Howell, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 16/877,104

(22) Filed: May 18, 2020

(65) Prior Publication Data
US 2020/0384247 A1 Dec. 10, 2020

Related U.S. Application Data

(62) Division of application No. 15/603,760, filed on May 24, 2017, now Pat. No. 10,653,873.
(Continued)

(51) Int. Cl.
*A61M 29/00* (2006.01)
*A61M 25/06* (2006.01)
(Continued)

(52) U.S. Cl.
CPC ........ *A61M 29/00* (2013.01); *A61M 25/0023* (2013.01); *A61M 25/0662* (2013.01);
(Continued)

(58) Field of Classification Search
CPC .............. A61M 29/00; A61M 25/0023; A61M 25/0662; A61M 25/005;
(Continued)

(56) References Cited

U.S. PATENT DOCUMENTS

| 4,601,713 A | 7/1986 | Fuqua |
| 4,656,070 A | 4/1987 | Nyberg et al. |

(Continued)

FOREIGN PATENT DOCUMENTS

| IT | 1393665 | 5/2012 |
| JP | H09501594 | 2/1997 |

(Continued)

OTHER PUBLICATIONS

European Search Report dated Jan. 29, 2020 for EP17803478.1.
(Continued)

*Primary Examiner* — Erich G Herbermann
(74) *Attorney, Agent, or Firm* — Dorsey & Whitney LLP

(57) ABSTRACT

Expandable introducer systems are provided. An expandable introducer system can include an expandable introducer, an expander, a support member, and/or an exchange dilator. The expandable introducer may be configured to transition from an unexpanded configuration to an expanded configuration. For example, the expander may be displaced through the expandable introducer and transition the expandable introducer from the unexpanded configuration to the expanded configuration. The support member may be disposed within the expandable introducer that is in the expanded configuration to maintain the expandable introducer in the expanded configuration.

19 Claims, 13 Drawing Sheets

Related U.S. Application Data

(60) Provisional application No. 62/382,001, filed on Aug. 31, 2016, provisional application No. 62/341,980, filed on May 26, 2016.

(51) Int. Cl.
*A61M 25/00* (2006.01)
*B29C 48/23* (2019.01)

(52) U.S. Cl.
CPC ...... *B29C 48/23* (2019.02); *A61B 2560/0406* (2013.01); *A61M 25/005* (2013.01); *A61M 2025/0024* (2013.01)

(58) Field of Classification Search
CPC .. A61M 2560/0406; A61M 2025/0024; A61M 29/02; A61M 2025/0681; A61M 2025/0025; A61M 25/0026; A61M 2029/025; B29C 48/23
USPC ......................................................... 606/191
See application file for complete search history.

(56) References Cited

U.S. PATENT DOCUMENTS

| | | | |
|---|---|---|---|
| 4,705,501 A | 11/1987 | Wigness et al. | |
| 4,738,666 A | 4/1988 | Fuqua | |
| 4,841,977 A | 6/1989 | Griffith et al. | |
| 4,921,479 A | 5/1990 | Grayzel | |
| 4,961,731 A | 10/1990 | Poncy | |
| 5,219,335 A | 6/1993 | Willard et al. | |
| 5,318,588 A | 6/1994 | Horzewski et al. | |
| 5,342,350 A | 8/1994 | Amiel | |
| 5,406,871 A | 4/1995 | Lambert, Jr. | |
| 5,464,398 A | 11/1995 | Haindl | |
| 5,599,307 A | 2/1997 | Bacher et al. | |
| 5,674,198 A | 10/1997 | Leone | |
| 5,676,659 A | 10/1997 | McGurk | |
| 5,827,243 A | 10/1998 | Palestrant | |
| 5,833,658 A | 11/1998 | Levy et al. | |
| 5,893,841 A | 4/1999 | Glickman | |
| 5,928,250 A | 7/1999 | Koike et al. | |
| 5,971,975 A | 10/1999 | Mills et al. | |
| 5,997,508 A | 12/1999 | Lunn et al. | |
| 6,090,072 A * | 7/2000 | Kratoska ............ | A61B 17/3439 604/164.01 |
| 6,117,105 A | 9/2000 | Bresnaham et al. | |
| 6,197,016 B1 | 3/2001 | Fourkas | |
| 6,312,374 B1 | 11/2001 | Von Hoffmann | |
| 6,312,443 B1 | 11/2001 | Stone | |
| 6,338,725 B1 | 1/2002 | Hermann et al. | |
| 6,585,719 B2 | 7/2003 | Wang | |
| 6,769,431 B2 | 8/2004 | Smith et al. | |
| 6,984,201 B2 | 1/2006 | Khaghani et al. | |
| 7,766,820 B2 | 8/2010 | Core | |
| 7,892,203 B2 | 2/2011 | Lenker | |
| 8,597,277 B2 | 12/2013 | Lenker et al. | |
| 8,690,936 B2 | 4/2014 | Nguyen et al. | |
| 8,764,704 B2 | 7/2014 | Lenker et al. | |
| 8,974,419 B2 | 3/2015 | Pini et al. | |
| 2001/0012950 A1 | 8/2001 | Nishtala et al. | |
| 2002/0032459 A1 | 3/2002 | Horzewski | |
| 2004/0087968 A1 | 5/2004 | Core | |
| 2004/0131808 A1 | 7/2004 | Schoenie et al. | |
| 2005/0080430 A1 | 4/2005 | Wright et al. | |
| 2005/0149105 A1 | 7/2005 | Leeflang et al. | |
| 2005/0222576 A1 | 10/2005 | Kick | |
| 2006/0052750 A1 | 3/2006 | Lenker et al. | |
| 2006/0135981 A1 * | 6/2006 | Lenker ................ | A61M 29/02 606/191 |
| 2006/0217755 A1 | 9/2006 | Eversull | |
| 2007/0119511 A1 | 5/2007 | Donohue et al. | |
| 2007/0167930 A1 | 7/2007 | Eversull et al. | |
| 2008/0200943 A1 | 8/2008 | Barker et al. | |
| 2008/0221552 A1 | 9/2008 | Leonard | |
| 2008/0243072 A1 | 10/2008 | Jenson et al. | |
| 2009/0076455 A1 * | 3/2009 | Pini .................... | A61M 25/0023 604/167.03 |
| 2009/0306701 A1 | 12/2009 | Porter | |
| 2010/0030162 A1 * | 2/2010 | Cremascoli ........ | A61M 25/0021 604/246 |
| 2010/0058201 A1 | 4/2010 | Hattangadi et al. | |
| 2010/0094392 A1 | 4/2010 | Nguyen et al. | |
| 2011/0144690 A1 | 6/2011 | Bishop et al. | |
| 2011/0245806 A1 | 10/2011 | Patterson | |
| 2012/0083877 A1 | 4/2012 | Nguyen et al. | |
| 2013/0150793 A1 | 6/2013 | Beissel et al. | |
| 2013/0184736 A1 | 7/2013 | Aman et al. | |
| 2014/0236123 A1 | 8/2014 | Birmingham et al. | |
| 2015/0174376 A1 | 6/2015 | Silva et al. | |
| 2016/0074067 A1 | 3/2016 | Furnish et al. | |
| 2016/0158502 A1 * | 6/2016 | Kume ................ | A61M 25/0662 604/510 |
| 2016/0213882 A1 * | 7/2016 | Fitterer ................ | A61M 25/01 |
| 2017/0340867 A1 | 11/2017 | Accisano, III | |

FOREIGN PATENT DOCUMENTS

| | | |
|---|---|---|
| WO | 199829026 | 7/1998 |
| WO | 2002089899 | 11/2002 |
| WO | 2006031619 | 3/2006 |
| WO | 2006031619 A8 | 8/2006 |
| WO | 2010075565 | 7/2010 |
| WO | 2013106134 | 7/2013 |
| WO | 2013106134 A1 | 7/2013 |

OTHER PUBLICATIONS

International Search Report and Written Opinion dated Aug. 8, 2017 for PTC/US2017/034157.
Office Action dated Apr. 17, 2019 for U.S. Appl. No. 15/603,760.
Office Action dated Oct. 24, 2019 for U.S. Appl. No. 15/603,760.
Vixtrex, 'Product Portfolio Summary', http:www.victrex.com/docs/literature-docs/Product%20Summary%20Card.pdf Retrieved Feb. 11, 2012.
European Search Report dated Aug. 28, 2013 for EP13175144.8.
Notice of Allowance dated Mar. 25, 2020 for U.S. Appl. No. 14/642,288.
Notice of Allowance dated Sep. 20, 2017 for U.S. Appl. No. 12/313,731.
Notice of Allowance dated Dec. 15, 2014 for U.S. Appl. No. 12/587,201.
Office Action dated Jan. 3, 2018 for U.S. Appl. No. 13/935,921.
Office Action dated Jan. 12, 2016 for U.S. Appl. No. 13/935,921.
Office Action dated Feb. 14, 2017 for U.S. Appl. No. 13/935,921.
Office Action dated Feb. 16, 2012 for U.S. Appl. No. 12/313,731.
Office Action dated Mar. 3, 2011 for U.S. Appl. No. 12/313,731.
Office Action dated Mar. 20, 2015 for U.S. Appl. No. 12/802,926.
Office Action dated Mar. 28, 2014 for U.S. Appl. No. 12/313,731.
Office Action dated Mar. 31, 2017 for U.S. Appl. No. 14/642,288.
Office Action dated Apr. 6, 2017 for U.S. Appl. No. 12/313,731.
Office Action dated Apr. 9, 2015 for U.S. Appl. No. 12/313,731.
Office Action dated Apr. 11, 2018 for U.S. Appl. No. 14/642,288.
Office Action dated Apr. 20, 2016 for U.S. Appl. No. 12/802,926.
Office Action dated May 18, 2016 for U.S. Appl. No. 12/313,731.
Office Action dated May 29, 2019 for U.S. Appl. No. 14/642,288.
Office Action dated Jun. 2, 2014 for U.S. Appl. No. 12/802,926.
Office Action dated Jun. 23, 2011 for U.S. Appl. No. 12/313,731.
Office Action dated Jul. 18, 2013 for U.S. Appl. No. 12/313,731.
Office Action dated Jul. 14, 2017 for U.S. Appl. No. 14/642,288.
Office Action dated Jul. 27, 2011 for U.S. Appl. No. 12/802,926.
Office Action dated Jul. 28, 2015 for U.S. Appl. No. 13/935,921.
Office Action dated Aug. 19, 2010 for U.S. Appl. No. 12/313,731.
Office Action dated Aug. 21, 2017 for U.S. Appl. No. 13/935,921.
Office Action dated Aug. 28, 2018 for U.S. Appl. No. 14/642,288.
Office Action dated Sep. 22, 2014 for U.S. Appl. No. 12/313,731.
Office Action dated Sep. 24, 2015 for U.S. Appl. No. 12/802,926.
Office Action dated Sep. 27, 2016 for U.S. Appl. No. 13/935,921.
Office Action dated Oct. 22, 2019 for U.S. Appl. No. 14/642,288.

(56) References Cited

OTHER PUBLICATIONS

Office Action dated Nov. 2, 2012 for U.S. Appl. No. 12/802,926.
Office Action dated Nov. 14, 2016 for U.S. Appl. No. 14/642,288.
Office Action dated Nov. 30, 2016 for U.S. Appl. No. 12/313,731.
Office Action dated Dec. 5, 2016 for U.S. Appl. No. 12/802,926.
Office Action dated Dec. 15, 2015 for U.S. Appl. No. 12/313,731.
Office Action dated Dec. 18, 2017 for U.S. Appl. No. 14/642,288.
Office Action dated Dec. 21, 2012 for U.S. Appl. No. 12/313,731.
Office Action dated Dec. 29, 2017 for U.S. Appl. No. 12/802,926.
PEEK (PolyetherEtherKetone) Specifications http://web.archive.org/web/2005036025200/http://www.boedeker.com/peek_p.htm, Mar. 6, 2005.

* cited by examiner

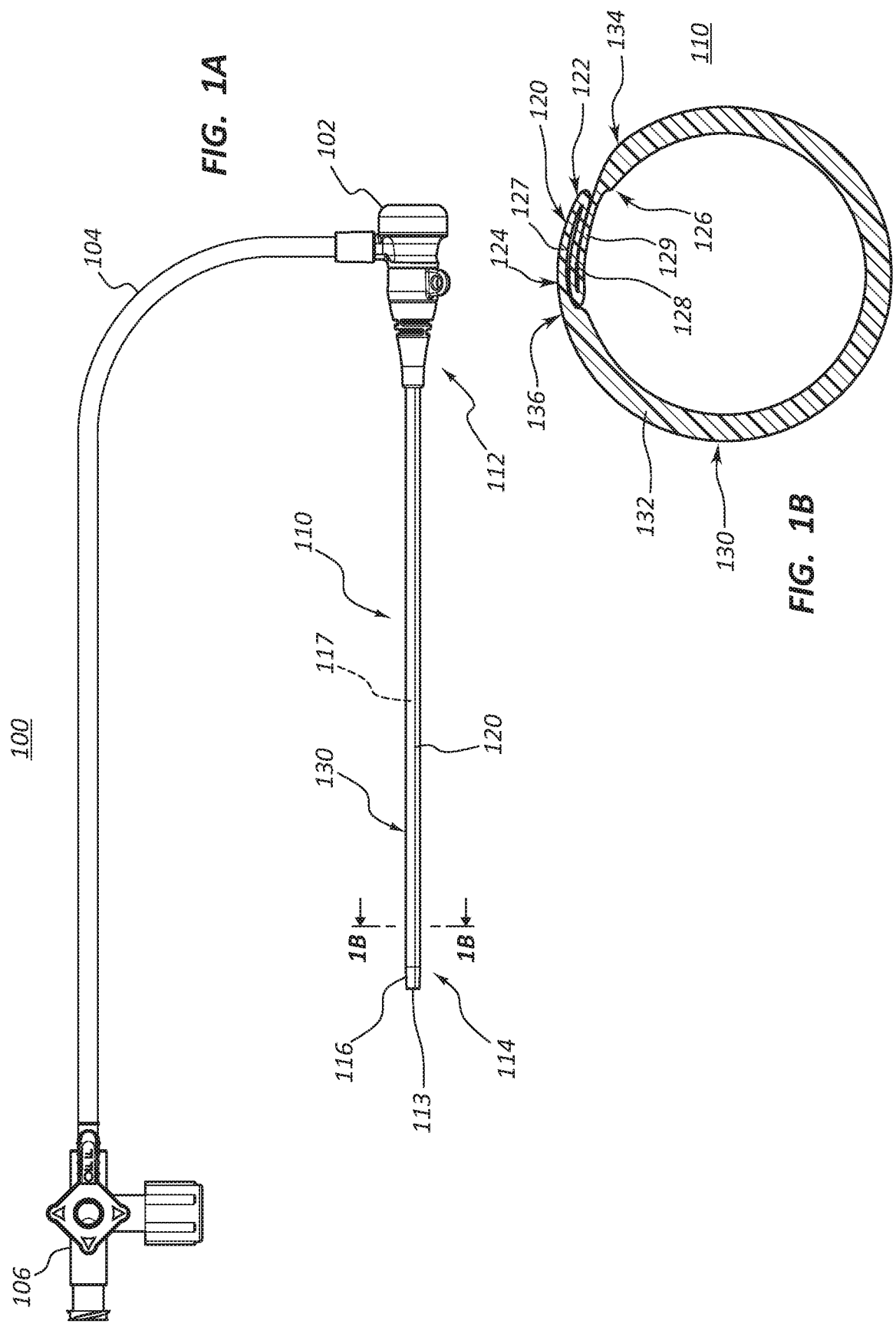

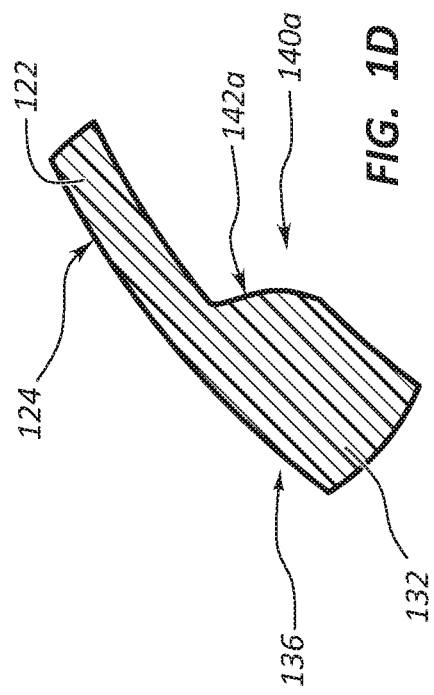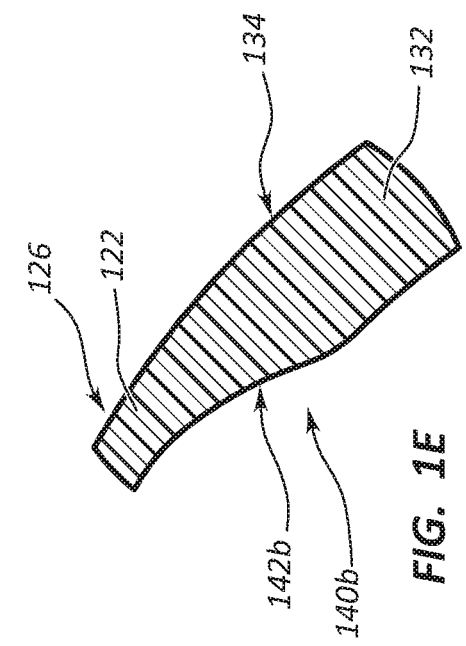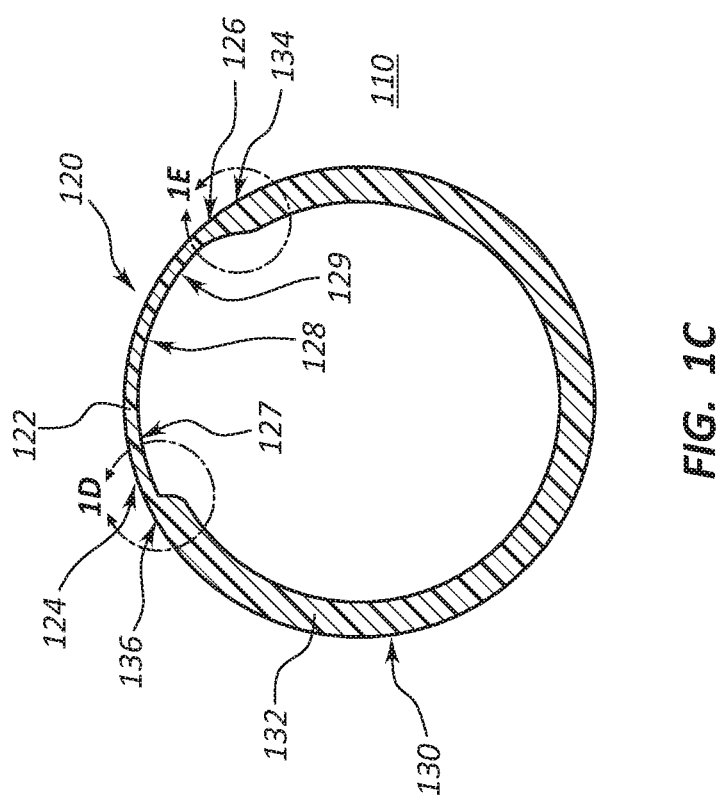

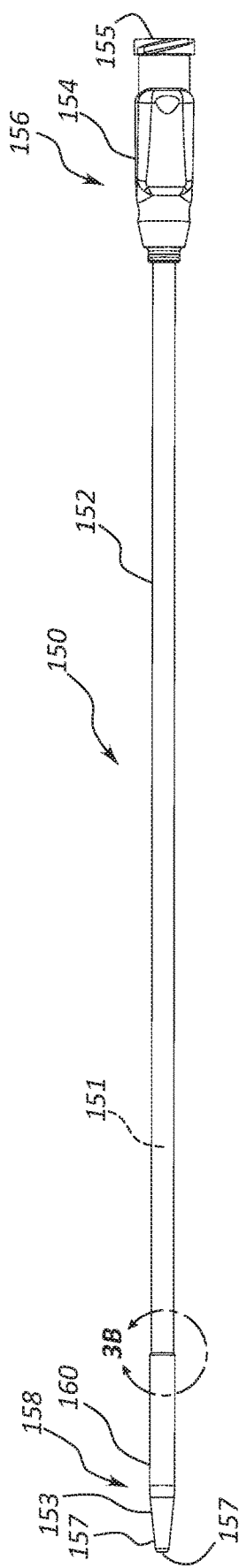
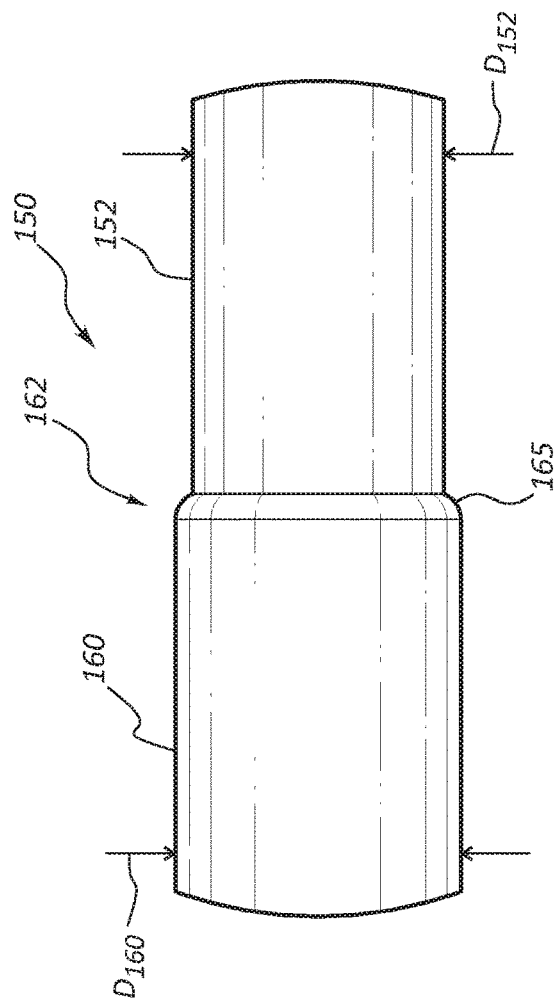
FIG. 3A
FIG. 3B

EXPANDABLE INTRODUCER ASSEMBLY

RELATED APPLICATIONS

This application is a divisional of U.S. patent application Ser. No. 15/603,760, filed on May 24, 2017 and titled, "Expandable Introducer Assembly," which claims the benefit of (1) U.S. Provisional Application No. 62/341,980, filed on May 26, 2016 and titled "EXPANDABLE INTRODUCER ASSEMBLY" and (2) U.S. Provisional Application No. 62/382,001, filed on Aug. 31, 2016 and titled "EXPANDABLE INTRODUCER ASSEMBLY," all of which are hereby incorporated by reference in their entireties.

TECHNICAL FIELD

The present disclosure relates generally to introducers. More specifically, the present disclosure relates to expandable introducers. This disclosure also relates to expanders, support members, and exchange dilators for use with expandable introducers. Related methods are also provided.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 1A is a top view of an expandable introducer assembly.

FIG. 1B is a cross-sectional view of the expandable introducer of FIG. 1A in an unexpanded configuration taken through plane 1B-1B.

FIG. 1C is a cross-sectional view of the expandable introducer of FIG. 1A in an expanded configuration.

FIG. 1D is a detail view of a portion of the expandable introducer of FIG. 1C taken through line 1D.

FIG. 1E is a detail view of another portion of the expandable introducer of FIG. 1C taken through line 1E.

FIG. 3A is a side view of an expander.

FIG. 3B is a detail view of the expander of FIG. 3A taken through line 3B.

DETAILED DESCRIPTION

Figure 2A:
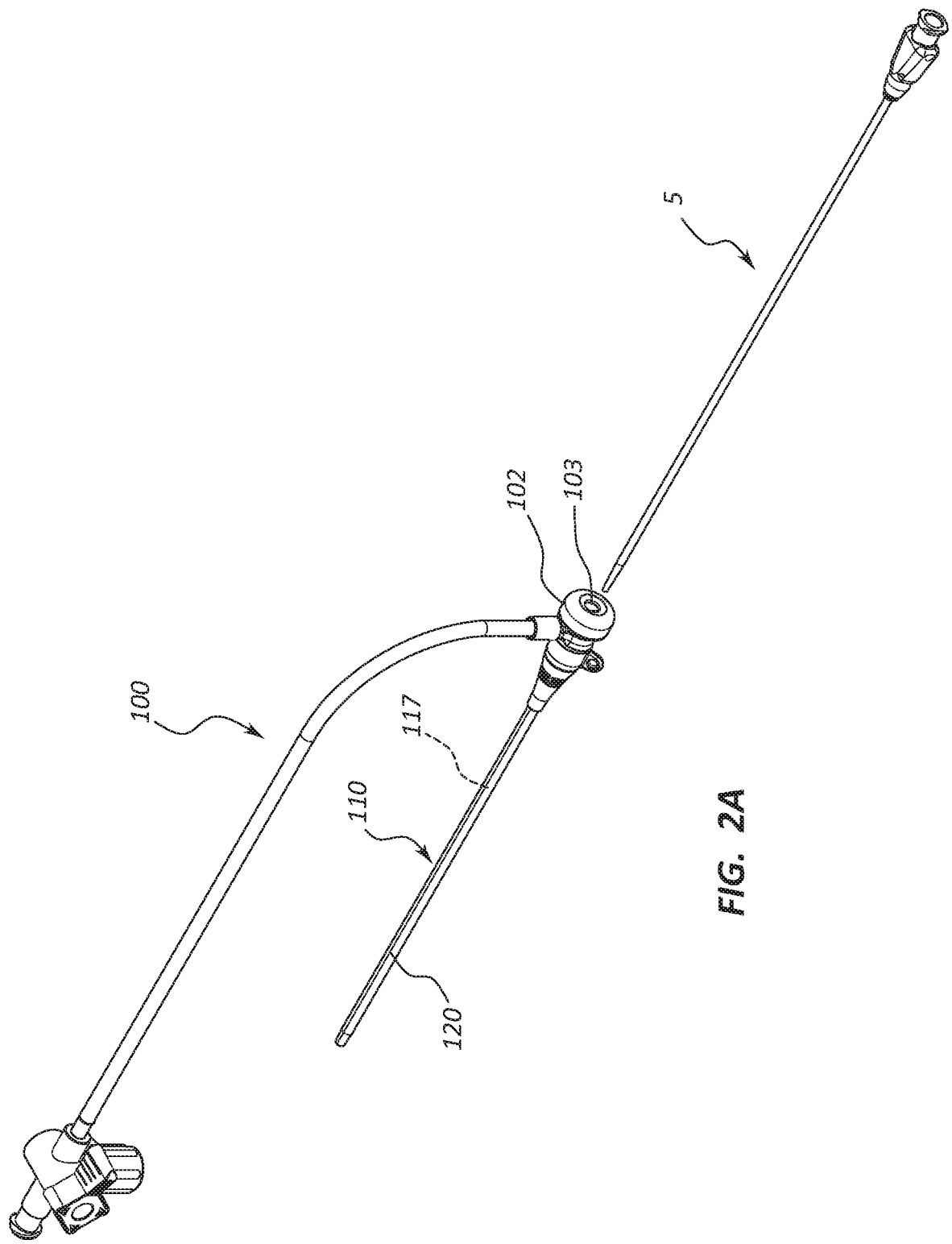
FIG. 2A is a perspective view of the expandable introducer assembly of FIG. 1A and a dilator in a first configuration.

The various embodiments disclosed herein generally relate to expandable introducer assemblies and systems. In some embodiments, an expandable introducer system may include an expandable introducer, an expander, a support member, and/or an exchange dilator. The expandable introducer may include an elongate member and an expandable member. The expander may be configured to be disposed through a lumen of the expandable introducer to expand or transition the expandable introducer from an unexpanded configuration to an expanded configuration. The support member may be configured to maintain the expandable introducer in the expanded configuration. In some embodiments, the expandable introducer may comprise a selectively expandable portion configured to expand or relax during use. In such embodiments, a support member and expander may be simultaneously inserted into an expandable introducer with the selectively expandable portion in an expanded state to expand the expandable introducer. The selectively expandable portion may then be relaxed to facilitate withdrawal of the expander, for example through a lumen of the support member. The exchange dilator may be configured to aid in the removal of the expandable introducer from a vessel of a subject and/or the disposition of a second larger fixed dilator or other suitable elongate medical device into the vessel of the subject.

It will be appreciated that various features are sometimes grouped together in a single embodiment, figure, or description thereof for the purpose of streamlining the disclosure. Many of these features may be used alone and/or in combination with one another.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" are opposite directional terms. For example, the distal end of a device or component is the end of the component that is farthest from the practitioner during ordinary use. The proximal end refers to the opposite end, or the end nearest the practitioner during ordinary use.

FIG. 1A is a top view of an expandable introducer assembly 100. As depicted, the assembly 100 can include an expandable introducer 110, a hub 102 coupled to a proximal end portion 112 of the expandable introducer 110, a sidearm catheter 104 coupled to and extending away from the hub 102 at a first end of the sidearm catheter 104, and a stopcock valve 106 coupled to a second end of the sidearm catheter 104.

The expandable introducer 110 includes an elongate member 130 and a distal end portion 114 that is disposed opposite the proximal end portion 112 along a longitudinal axis of the expandable introducer 110 and/or the elongate member 130. As depicted, the distal end portion 114 can include a tapered portion 116. In some embodiments, the tapered portion 116 may be shaped such that the expandable introducer 110 may be more easily disposed within a lumen (e.g., a vessel of a subject) as compared to an expandable introducer that lacks a tapered portion. Expandable introducers lacking tapered portions are also within the scope of this disclosure. The expandable introducer 110 can also include a lumen 117 extending between each of a proximal end of the hub 102 and a distal end 113 of the expandable introducer 110.

In certain embodiments, the expandable introducer 110 may be configured to transition from a first, unexpanded configuration to a second, expanded configuration. For example, in the unexpanded configuration, the expandable introducer 110 may have a first size and/or diameter (i.e., an unexpanded size and/or diameter). In the expanded configuration, the expandable introducer 110 may have a second size and/or diameter (i.e., an expanded size and/or diameter). In various embodiments, the first size may be about 5 French and the second size may be about 7 French. As such, the expandable introducer 110 may be configured to expand or transition from about 5 French to about 7 French (as discussed in further detail below).

In various other embodiments, the first size may be about 3 French to about 8 French, about 4 French to about 6 French, or another suitable size. In yet other various embodiments, the second size may be about 4 French to about 10 French, about 5 French to about 9 French, about 6 French to about 8 French, or another suitable size. Other combinations of the first and second sizes are also within the scope of this disclosure.

Throughout this disclosure, the expandable introducer 110, or at least a portion of the expandable introducer 110, may be described as having a 5 French size in the unexpanded configuration. Furthermore, the expandable introducer 110, or at least a portion of the expandable introducer 110, may be described as having a 7 French size in the expanded configuration. As can be appreciated by one of skill in the art, with the benefit of this disclosure, the sizes of the expandable introducer 110 in the unexpanded configuration and the expanded configuration may vary. Accordingly, any sizes of the expandable introducer 110 in the unexpanded configuration and the expanded configuration may be analogously applied to the descriptions of various embodiments throughout the present disclosure. In other words, though specific examples below may refer to 5 French as the unexpanded size and 7 French as the expanded size, introducers configured to transition between any unexpanded size and any expanded size are within the scope of this disclosure. Disclosure recited in connection with examples of specific sizes may analogously the applied to any other size.

In some embodiments, an elongate medical device for use in a diagnostic procedure may be displaceable through a 5 French introducer. In contrast, an elongate medical device for use in a therapeutic procedure may be displaceable through a 7 French dilator. In other words, the diagnostic elongate medical device, but not the therapeutic elongate medical device, may be displaceable through a 5 French introducer so as to access a vessel of a subject.

In various embodiments, the exchanging or switching of an introducer during a medical procedure may cause a spasm of a vessel of a subject, which may at least partially occlude the vessel. Such a vascular spasm may complicate or inhibit the exchanging of an introducer having a first size with an introducer having a second size (e.g., from a 5 French introducer to a 7 French introducer) during the medical procedure.

The expandable introducer 110 may expand at an expandable member 120. The expandable member 120 can be disposed along at least a portion of the elongate member 130 of the expandable introducer 110. As illustrated, the expandable member 120 can extend along a portion of the length of the elongate member 130, and the expandable member 120 can be substantially linear and straight. In some embodiments, the expandable member 120 may extend along only a portion of the length of the elongate member 130. For example, the expandable member 120 may extend from the distal end 113 of the expandable member 120 to a position at about the midpoint of the elongate member 130 (e.g., about halfway along the length of the elongate member 130).

In certain embodiments, the expandable member 120 may extend from the distal end 113 of the expandable member 120 along a distal portion of the expandable introducer 110. In such an embodiment, the proximal portion of the expandable introducer 110 may have a diameter that is greater than a diameter of the distal portion of the expandable introducer 110 when the expandable introducer 110 is in the unexpanded configuration. For example, the distal portion of the expandable introducer 110, which comprises the expandable member 120, may be 5 French in the unexpanded configuration and 7 French in the expanded configuration. In contrast, the proximal portion of the expandable introducer 110, which lacks the expandable member 120, may be 7 French and may not change in size when the expandable member 120 transitions from the unexpanded configuration to the expanded configuration. As discussed above, any suitable combination of sizes of the expandable introducer in each of the unexpanded configuration and the expanded configuration is within the scope of this disclosure.

For ease of describing the expandable introducer 110, the expandable member 120 and the elongate member 130 may be referred to as separate components of the expandable introducer 110 in the present disclosure. As depicted in the figures (e.g., FIGS. 1A-1E) and as described in portions of this disclosure; however, the expandable member 120 can be integral with, or a segment of, the elongate member 130. Accordingly, embodiments wherein the expandable member 120 and the elongate member 130 are discrete, and embodiments wherein the expandable member 120 and the elongate member 130 are integral, are both within the scope of this disclosure. Thus, references herein to an expandable introducer member 120 should not be understood as only defining the expandable introducer member 120 as a separate component from the elongate member 130, rather such references include embodiments wherein the expandable member 120 comprises a segment or portion of the elongate member 130 and/or wherein these components are integrally formed from a continuous material (for example by extrusion of a tube comprising these components).

In some embodiments, the expandable member 120 may extend from the distal end 113 along at least about one-fifth of the length of the elongate member 130, along at least about one-fourth of the length of the elongate member 130, along at least about one-half of the length of the elongate member 130, along at least about two-thirds of the length of the elongate member 130, or along another suitable fraction of the length of the elongate member 130. In various embodiments, the expandable member 120 may be bent, curved, wavy, or another suitable shape.

FIG. 1B is a cross-sectional view of a portion of the expandable introducer 110 in the unexpanded configuration. FIG. 1C is a cross-sectional view of the expandable introducer 110 in the expanded configuration. As illustrated, the elongate member 130 can comprise a wall such as a first wall 132, wherein the first wall 132 extends circumferentially between a first end 134 and a second end 136. The expandable member 120 can be disposed between each of the first end 134 and the second end 136. In some embodiments, the elongate member 130 and the expandable member 120 may be integral. For example, each of the elongate member 130 and the expandable member 120 may be formed from a single piece of material. In some other embodiments, the elongate member 130 and the expandable member 120 may be discrete or separate. For example, the elongate member 130 may be formed from a first piece of material, the expandable member 120 may be formed from a second piece of material, and the discrete elongate member 130 and expandable member 120 may be coupled to each other.

As illustrated, the expandable member 120 can comprise a wall such as a second wall 122, wherein the second wall 122 extends between a first end 124 and a second end 126. Furthermore, the expandable member 120 can comprise a first or outer panel 127, a second or medial panel 128 coupled to the first panel 127, and a third or inner panel 129 coupled to the second panel 128. In certain embodiments, each of the first, second, and third panels 127, 128, 129 may be integral. In certain other embodiments, each of the first, second, and third panels 127, 128, 129 may be discrete. In yet other certain embodiments, a subset (i.e., two) of each of the first, second, and third panels 127, 128, 129 may be integral and the remaining panel may be discrete. For example, the first and second panels 127, 128 may be integral and the third panel 129 may be discrete.

The wall 132 of the elongate member 130 has a thickness. The wall 122 of the expandable member 120 also has a thickness. As depicted, the thickness of the wall 132 is greater than the thickness of the wall 122. In some embodiments, the thickness of the wall 132 may be substantially equal to the thickness of the wall 122. In some other embodiments, the thickness of the wall 132 may be less than the thickness of the wall 122. With continued reference to FIG. 1B, the thickness of the wall 122 may be about one-third of the thickness of the wall 132. In such a configuration, upon pleating or folding of the first, second, and third panels 127, 128, 129 (i.e., when the expandable introducer 110 is in the unexpanded configuration, as illustrated) the thickness of the expandable member 120 in the unexpanded configuration is substantially equal to the thickness of the wall 132.

In some embodiments, when the expandable introducer 110 is in the unexpanded configuration, a first fold or pleat may be formed between the first or outer panel 127 and the second or medial panel 128. Furthermore, a second fold or pleat may be formed between the medial panel 128 and the third or inner panel 129 such that each of the first, second, and third panels 127, 128, 129 is layered against each other.

In certain embodiments, the expandable introducer 110 may be formed from a urethane (e.g., TECOFLEX™, an aliphatic polyether-based thermoplastic polyurethane) or another suitable material. A softening agent may also be added to or used with the urethane or other suitable material (e.g., KETAMIDE™, MOLDWIZ®, etc.). The expandable introducer 110 may be formed or manufactured by extrusion or any other suitable method. In various embodiments, the expandable member 120 may be folded or pleated by disposing a mandrel having a desired shape against an interior surface of the expandable introducer 110 while an exterior surface of the expandable introducer 110 is constrained radially inward by a constraining device (e.g., a tube). Upon removal of the mandrel and/or the constraining device, the expandable member 120 may be folded or pleated into the unexpanded configuration (as depicted, for example, in FIG. 1B).

In some embodiments, the folding of the expandable member 120 may be conducted or performed via a heat treatment. To avoid or prevent coupling or welding of the first, second, and/or third panels 127, 128, 129 (i.e., to each other) during the heat treatment, the material forming the expandable member 120 may be coated. For example, the material may be coated with at least one of polytetrafluoroethylene (PTFE), quartz, silicone oil, or another suitable coating.

In certain embodiments, at least a portion of the expandable introducer 110 may be dipped in a silicone oil prior to being folded into the unexpanded configuration. In certain other embodiments, at least a portion of the expandable introducer 110 may be soaked in a silicone oil prior to being folded. Such treatment of the expandable introducer 110 may prevent welding of the first, second, and/or third panels 127, 128, 129 during the heat treatment, as discussed above.

In various embodiments, a layer of a material such as a PTFE-based formula (e.g., TEFLON™) and/or a quartz may be deposited on at least a portion of an exterior surface of the expandable introducer 110. The layer (e.g., a thin layer) of the PTFE-based formula or the quartz can be deposited by a plasma process.

The fluoropolymer layer may also prevent welding of the first, second, and/or third panels 127, 128, 129 during the heat treatment. The coating and/or the co-extruded layer may prevent the expandable introducer 110 from tearing, stretching, and/or otherwise deforming during the transition from the unexpanded configuration to the expanded configuration.

At about room temperature, the material from which the expandable introducer 110 is formed may be rigid or stiff. At about body temperature, the material from which the expandable introducer 110 is formed may be less rigid or stiff. For example, upon disposition of at least a portion of the expandable introducer 110 within a vessel of a subject, the material from which the expandable introducer 110 is formed may soften or become pliable. As such, the expandable introducer 110 may be configured to more easily transition from the unexpanded configuration to the expanded configuration (i.e., when the expandable introducer 110 is at about body temperature). The enhanced pliability of the material at about body temperature may also prevent the expandable introducer 110 from tearing, stretching, and/or otherwise deforming during the transition from the unexpanded configuration to the expanded configuration.

FIGS. 1D and 1E are cross-sectional detail views of portions of the expandable introducer 110. As illustrated in FIG. 1D, the expandable introducer 110 can include a first transition portion 140a, and as illustrated in FIG. 1E, the expandable introducer 110 can further include a second transition portion 140b. The first transition portion 140a can be disposed between each of the second end 136 of the wall 132 and the first end 124 of the wall 122. The second transition portion 140b can be disposed between each of the second end 126 of the wall 122 and the first end 134 of the wall 132. The transition portion 140a can include a first shoulder 142a, and the transition portion 140b can include a second shoulder 142b. As depicted, the shoulders 142a, 142b can be disposed on an inner surface of the transition portions 140a, 140b. In some embodiments, the shoulders 142a, 142b may be disposed on an outer surface of the transition portions 140a, 140b. The expandable introducer 110 may also be described as not having transition portions 140a, 140b; however, the expandable introducer 110 may still include shoulders 142a, 142b. For example, the shoulders 142a, 142b may be portions or extensions of the expandable member 120 and/or the elongate member 130.

As depicted, the shoulder 142a can be configured or shaped differently than the shoulder 142b. Stated another way, the shoulder 142a and the shoulder 142b may be asymmetric. Such a configuration may bias the fold of the expandable member 120 to one side or in one direction. The slope of the shoulder 142a, as illustrated, is greater than the slope of the shoulder 142b. In other words, the slope of the shoulder 142b is more gradual than the slope of the shoulder 142a. The shape of the shoulder 142a may be configured to receive a fold of the wall 122 of the expandable member 120 when the expandable introducer 110 is disposed in the unexpanded configuration. Accordingly, the diameter of an outside surface of the expandable introducer 110 in the unexpanded configuration may be substantially constant or uniform. Likewise, the diameter of an inside surface of the expandable introducer 110 in the unexpanded configuration may also be substantially constant or uniform.

Figure 2B:
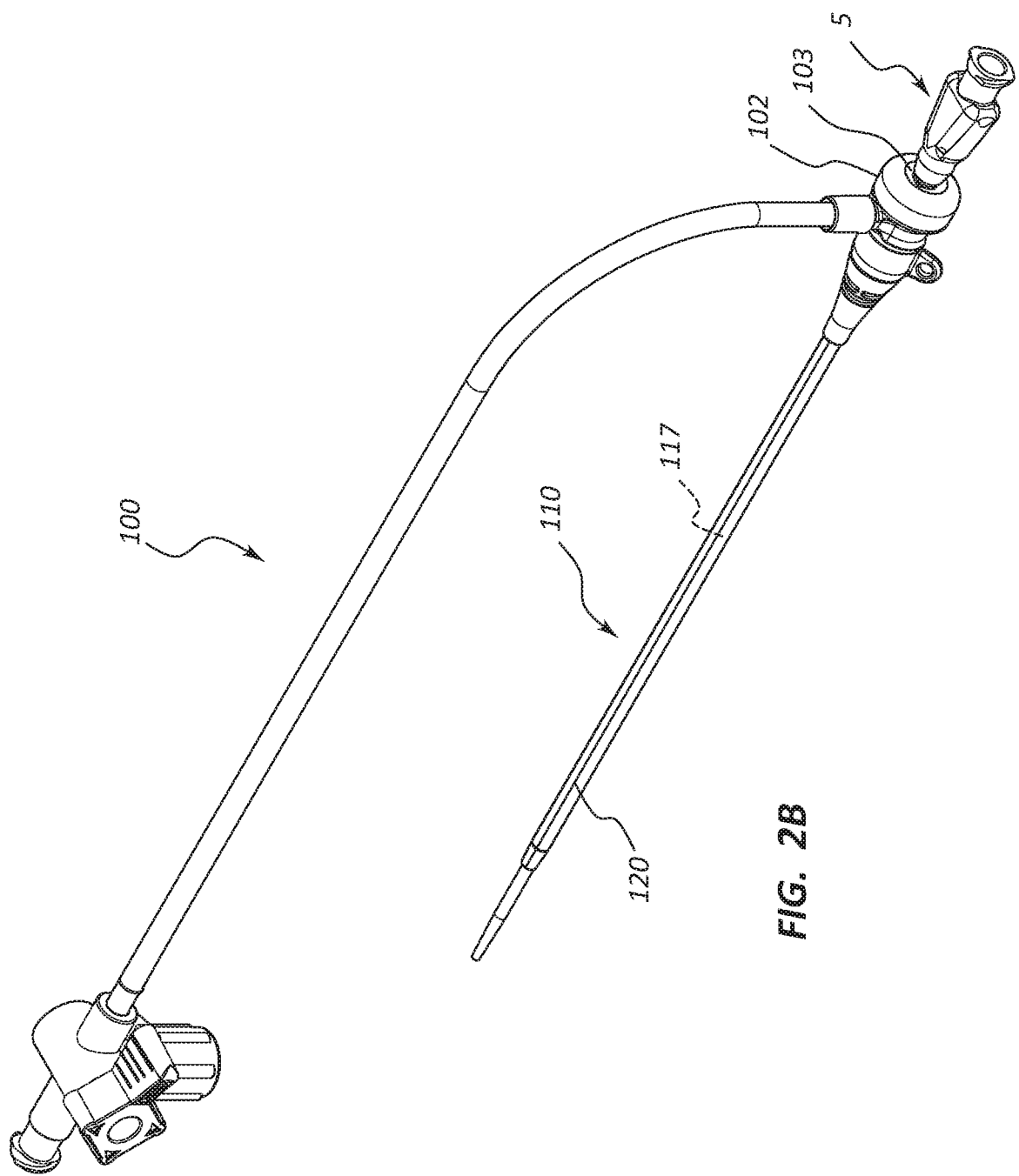
FIG. 2B is a perspective view of the expandable introducer and the dilator of FIG. 2A in a second configuration.

FIGS. 2A and 2B are perspective views of the expandable introducer assembly 100 and a dilator 5. In the illustrated embodiment, the expandable introducer 110 is in the unexpanded configuration, and the expandable introducer 110 is configured to expand or transition from a 5 French introducer (i.e., in the unexpanded configuration) to a 7 French introducer (i.e., in the expanded configuration). As discussed above, other sizes of expandable introducers are also within the scope of this disclosure.

In some embodiments, the expandable introducer 110 may be configured to receive a dilator 5. For example, the dilator 5 may be a 5 French dilator and the dilator 5 may be displaced (e.g., by a practitioner) through the lumen 117 of the expandable introducer 110. An opening 103 at the distal end of the hub 102 may be configured to receive the dilator 5. The dilator 5 may then pass through a lumen of the hub 102 and into the lumen 117 of the expandable introducer 110. FIG. 2A depicts the dilator 5 before the dilator 5 has been disposed in the expandable introducer 110 (or after the dilator 5 has been removed from the expandable introducer 110). FIG. 2B depicts the dilator 5 disposed within the expandable introducer 110. As illustrated, the expandable introducer 110 remains in the unexpanded configuration upon disposition of the dilator 5 within the lumen 117 of the expandable introducer 110.

The dilator 5 may be more rigid than the expandable introducer 110. For example, the dilator 5 may be formed from a material that is more rigid than the material from which the expandable introducer 110 is formed. A wall of the dilator 5 may also, or alternatively, be thicker than the walls of the expandable introducer 110.

FIG. 3A is a side view of an expander 150. The expander 150 can include an elongate member 152. A hub 154 can be disposed at or coupled to a proximal end portion 156 of the expander 150. An expander member 160 may be disposed at or coupled to a distal end portion 158 of the expander 150. Furthermore, a lumen 151 may be disposed within at least a portion of the length of the expander 150. For example, the lumen 151 may extend between a proximal end 155 and a distal end 157 of the expander 150.

In some embodiments, the expander member 160 may be disposed around at least a portion of an outer surface of the elongate member 152. For example, the expander member 160 may be disposed around the entire outer surface of the elongate member 152. The expander member 160 can include a tapered portion 153. The tapered portion 153 may aid or enhance the disposition of the expander 150 into an opening or a lumen as compared to an expander 150 that lacks a tapered portion. In certain embodiments, each of the components or a subset of the components of the expander 150 (e.g., the elongate member 152 and the expander member 160) may be integral. For example, the elongate member 152 and the expander member 160 may be formed from a single piece of material. In certain other embodiments, each of the components or a subset of the components of the expander 150 may be discrete. For example, the elongate member 152 may be formed from a first piece of material, and the expander member 160 may be formed from a second piece of material. The discrete elongate member 152 and expander member 160 may then be coupled or fixedly coupled to each other. Expander members lacking a tapered portion are also within the scope of this disclosure.

In some embodiments the expander member 160 may comprise a balloon or other inflatable or expandable member. Such an expander member 160 may be configured to be selectively expanded or relaxed during use. For example, the expander member 160 may be advanced through an expandable introducer (such as 110 of FIG. 1A) in an expanded configuration to expand the introducer. The expander member 160 could then be relaxed to a smaller diameter to facilitate removal of the expander 150 from the expandable introducer. In some instances, a selectively expandable expander member 160 may allow for simultaneous introduction of an expander 150 and a support member (such as support member 170 discussed further below). The expander member 160 may be in an expanded configuration and extending from a distal end of a support member, with the elongate member 152 disposed within a lumen of the support member. The expander 150 and support member could be advanced along an expandable introducer to expand the expandable introducer. The expander member 160 could then be relaxed to a smaller diameter to allow the expander member 160 to be removed through the lumen of the support member without withdrawing the support member 160. In some instances the expander member 160 may thus have a larger outside diameter than an inside diameter of the support member lumen when the expander member is expanded and a smaller outside diameter than the inside diameter of the support member lumen when the expander member 160 is relaxed or deflated.

FIG. 3B provides a detail view of a portion of the expander 150 at a junction of a proximal end portion 162 of the expander member 160. A ridge or annular ridge 165 can be disposed at the proximal end portion 162. As depicted, the ridge 165 can be rounded. In some embodiments, the ridge 165 may be blunt, tapered, or otherwise suitably shaped.

As depicted, a maximum diameter of the elongate member 152 (e.g., diameter $D_{152}$) is less than a maximum diameter of the expander member 160 (e.g., diameter $D_{160}$). Accordingly, upon passage of the expander 150 into a lumen (e.g., a lumen of an expandable introducer), friction between an outer surface of the expander 150 and an inner surface of the lumen may be substantially limited or reduced to only that associated with a portion of the expander 150 (i.e., the portion of the expander member 160 having the maximum diameter $D_{160}$). Such a configuration may ease or enhance the displacement of the expander 150 through the lumen of the expandable introducer as compared to an expander that has a substantially constant diameter along its entire length.

Figure 4A:
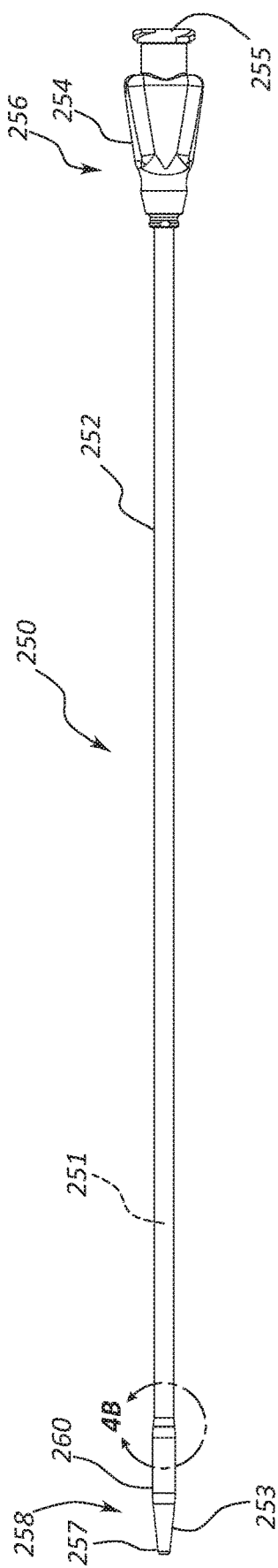
FIG. 4A is a side view of another embodiment of an expander.
Figure 4B:
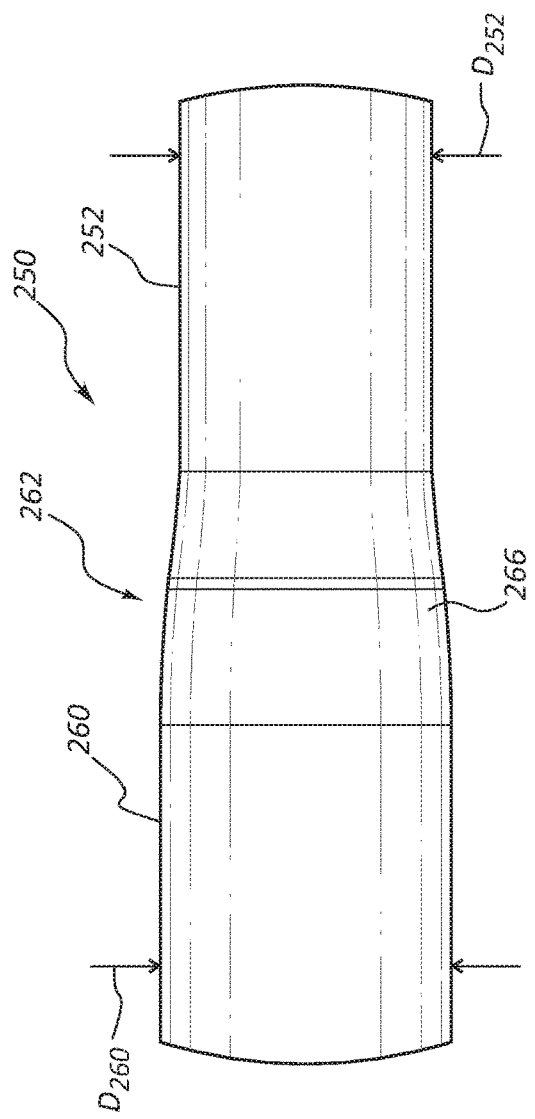
FIG. 4B is a detail view of the expander of FIG. 4A taken through line 4B.

FIGS. 4A and 4B depict an embodiment of an expander 250 that resembles the expander 150 described above in certain respects. Accordingly, like features are designated with like reference numerals, with the leading digits incremented to "2." For example, the embodiment depicted in FIGS. 4A and 4B includes an expander member 260 that may, in some respects, resemble the expander member 160 of FIGS. 3A and 3B. Relevant disclosure set forth above regarding similarly identified features thus may not be repeated hereafter. Moreover, specific features of the expander 150 and related components shown in FIGS. 3A and 3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the expander 250 and related components depicted in FIGS. 4A and 4B. Any suitable combination of the features, and variations of the same, described with respect to the expander 150 and related components illustrated in FIGS. 3A and 3B can be employed with the expander 250 and related components of FIGS. 4A and 4B, and vice versa. This pattern of disclosure applies equally to further embodiments depicted in subsequent figures and described hereafter, wherein the leading digits may be further incremented. Furthermore, this pattern of disclosure applies equally to further embodiments of other assemblies, devices, and components depicted and described herein (e.g., expandable introducer assemblies, expandable introducers, expandable members, etc.).

FIG. 4A is a side view of the expander 250. The expander 250 can include an elongate member 252. A hub 254 can be disposed at or coupled to a proximal end portion 256 of the expander 250. The expander member 260 may be disposed at or coupled to a distal end portion 258 of the expander 250. Furthermore, a lumen 251 may be disposed within at least a portion of the length of the expander 250. For example, the lumen 251 may extend between a proximal end 255 and a distal end 257 of the expander 250.

In some embodiments, the expander member 260 may be disposed around at least a portion of an outer surface of the elongate member 252. For example, the expander member 260 may be disposed around the entire outer surface of the elongate member 252. The expander member 260 can include a tapered portion 253. As discussed above in reference to the tapered portion 153, the tapered portion 253 may aid or enhance the disposition of the expander 250 into an opening or a lumen as compared to an expander 250 that lacks a tapered portion. In certain embodiments, each of the components or a subset of the components of the expander 250 (e.g., the elongate member 252 and the expander member 260) may be integral. For example, the elongate member 252 and the expander member 260 may be formed from a single piece of material. In certain other embodiments, each of the components or a subset of the components of the expander 250 may be discrete. For example, the elongate member 252 may be formed from a first piece of material, and the expander member 260 may be formed from a second piece of material. The discrete elongate member 252 and expander member 260 may then be coupled or fixedly coupled to each other.

FIG. 4B provides a detail view of a portion of the expander 250 at a junction of a proximal end portion 262 of the expander member 260. A reverse tapered portion or annular reverse tapered portion 266 can be disposed at the proximal end portion 262. In some embodiments, upon displacement of the expander 250 through a lumen of an expandable introducer, a user may displace or extend the expander member 260 beyond a distal end of the expandable introducer. The reverse tapered portion 266 may aid in redisposing the expander member 260 within the lumen of the expandable introducer. For example, upon proximal displacement of the expander 250 relative to the expandable introducer, the reverse tapered portion 266 may ease the disposition of the expander member 260 into the lumen of the expandable introducer.

As with the expander member 160 discussed above, the expander member 260 may comprise an inflatable balloon or other expandable member. Such an expander member 260 could be used simultaneously with a support member analogous to the expander member 160 described above.

As depicted, a maximum diameter of the elongate member 252 (e.g., diameter $D_{252}$) is less than a maximum diameter of the expander member 260 (e.g., diameter $D_{260}$). Accordingly, upon passage of the expander 250 into a lumen (e.g., a lumen of an expandable introducer), friction between an outer surface of the expander 250 and an inner surface of the lumen may be substantially limited or reduced to that associated with only a portion of the expander 250 (i.e., the portion of the expander member 260 having the maximum diameter $D_{260}$). Such a configuration may ease the displacement of the expander 250 through the lumen of the expandable introducer as compared to an expander that has a substantially constant diameter along its entire length.

With reference to FIGS. 3A and 4A, the expander member 160 may be longer than the expander member 260. The longer expander member 160 may be prevented from fully extending distally of the distal end 113 of the expandable introducer 110. In some embodiments, the shorter expander member 260 may be fully extended distally of the distal end 113 of the expandable introducer 110; however, the reverse tapered portion 266 may allow the expander member 260 to be proximally displaced within the expandable introducer 110. Such configurations may prevent or limit the distal end 113 and/or the distal end portion 114 of the expandable introducer 110 from being crimped, folded, or otherwise damaged during use of the expander member 160, 260. For example, the reverse tapered portion 266 can allow the expander member 260 to be proximally displaced within the expandable introducer 110 without crimping, folding, or damaging the distal end 113 and/or the distal end portion of the expandable introducer 110.

Figure 5A:
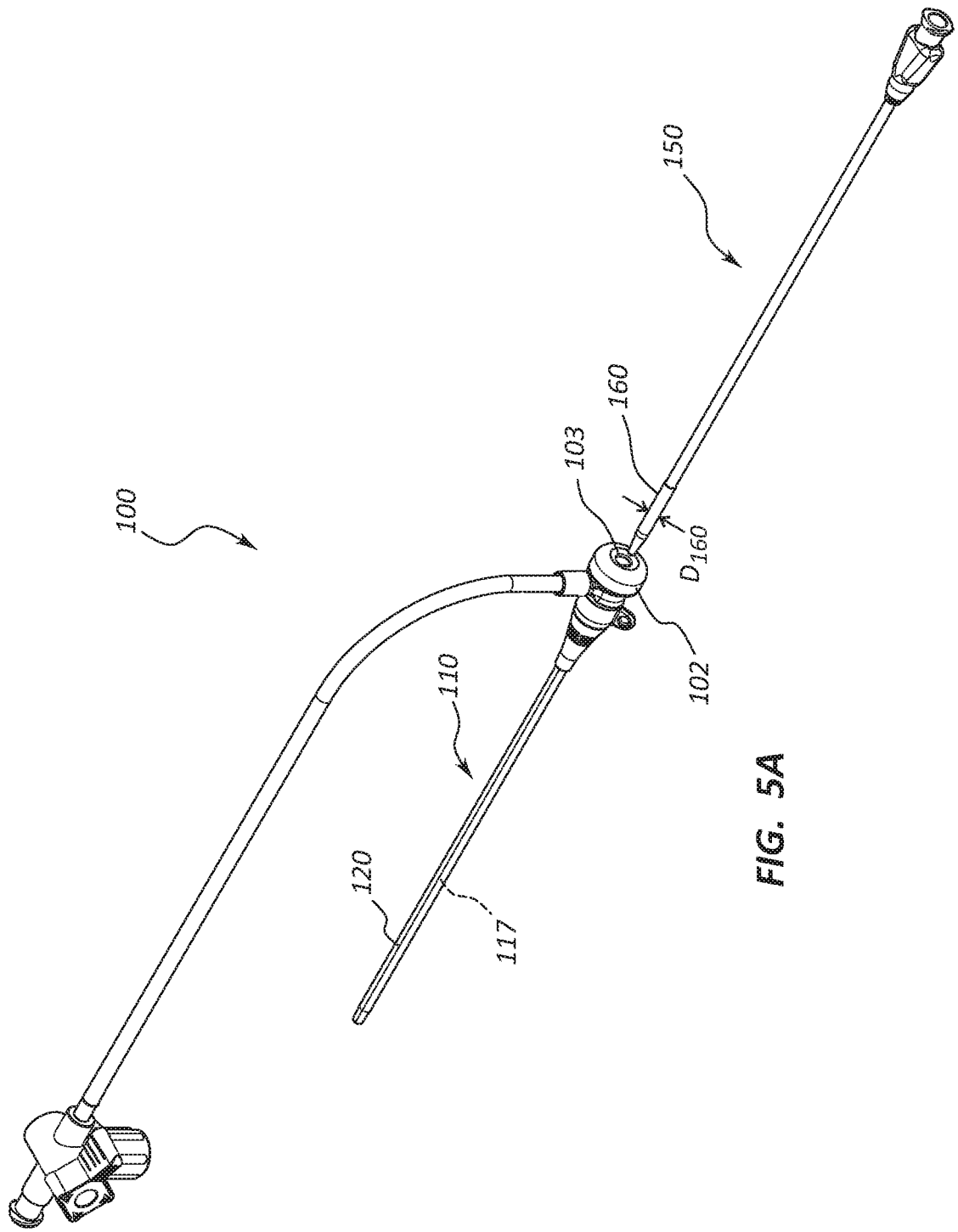
FIG. 5A is a perspective view of the expandable introducer assembly of FIG. 1A and the expander of FIG. 3A in a first configuration.
Figure 5B:
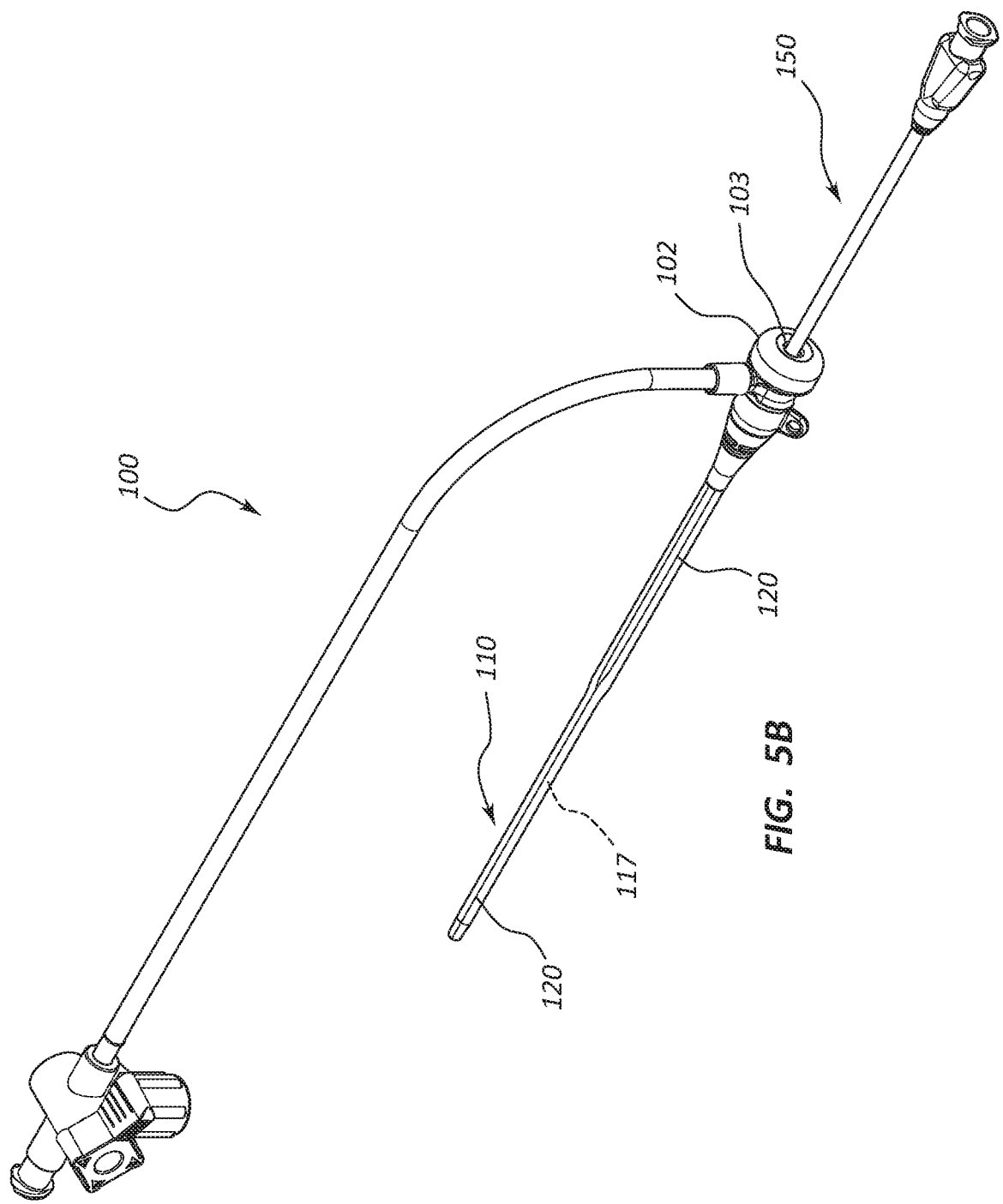
FIG. 5B is a perspective view of the expandable introducer assembly and the expander of FIG. 5A in a second configuration.
Figure 5C:
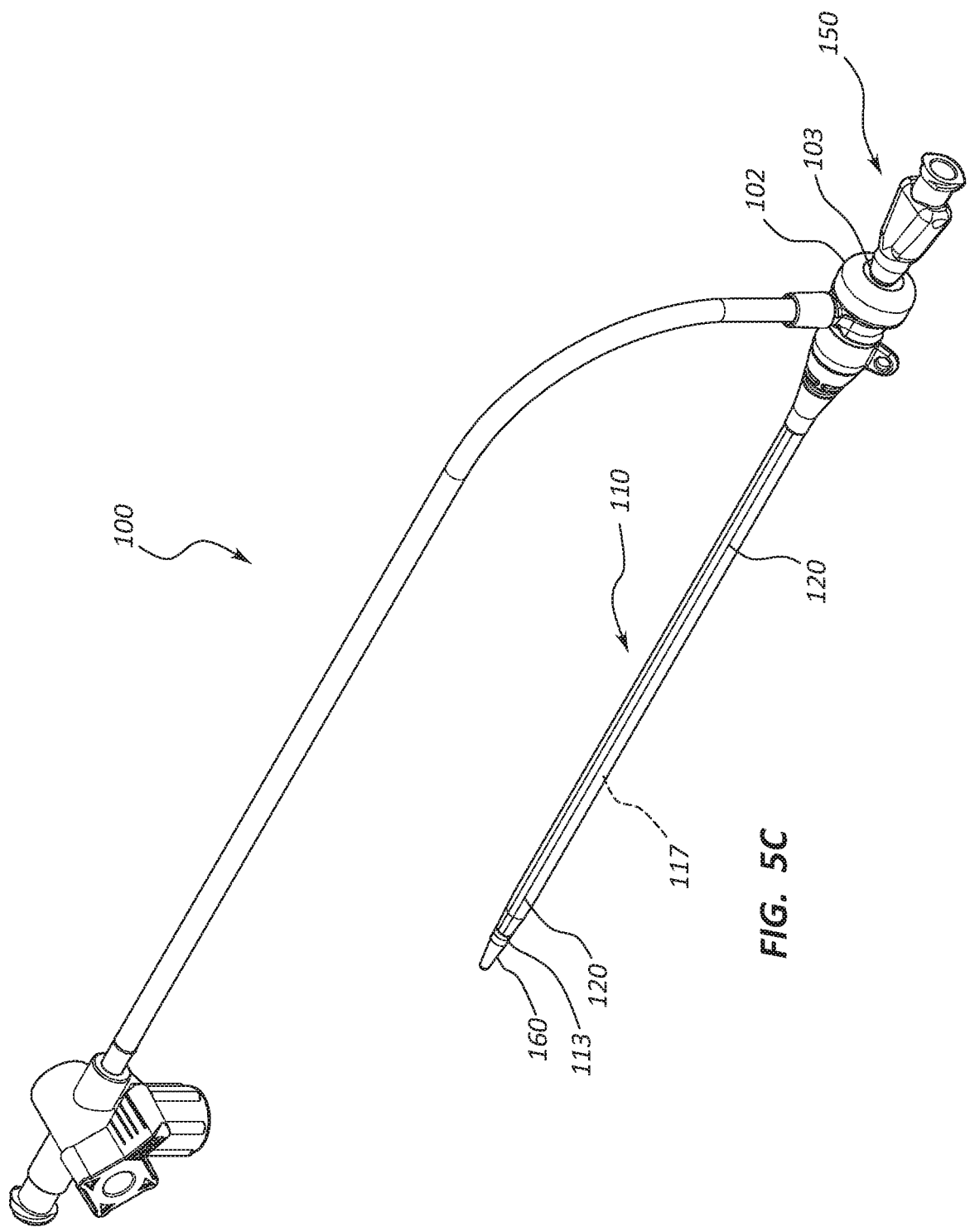
FIG. 5C is a perspective view of the expandable introducer assembly and the expander of FIG. 5A in a third configuration.

FIGS. 5A-5C are perspective views of the expandable introducer assembly 100 and the expander 150. In the illustrated embodiment of FIG. 5A, the expandable introducer 110 is in the unexpanded configuration. Accordingly, the expandable member 120 is in the unexpanded configuration. The expandable introducer 110 is configured to expand or transition from a 5 French introducer (i.e., in the unexpanded configuration) to a 7 French introducer (i.e., in the expanded configuration). Again, as discussed above, other sizes of expandable introducers are also within the scope of this disclosure.

In some embodiments, the expandable introducer 110 may be configured to receive the expander 150. For example, the expander 150 may be disposed within and/or displaced through (e.g., by a practitioner) the lumen 117 of the expandable introducer 110. The opening 103 at the proximal end of the hub 102 may be configured to receive the expander 150. The expander 150 may then pass through a lumen of the hub 102 and into the lumen 117 of the expandable introducer 110. FIG. 5A depicts the expander 150 proximal of the expandable introducer 110, such as before the expander 150 has been disposed in the expandable introducer 110 (or after the expander 150 has been removed from the expandable introducer 110).

FIG. 5B depicts the expander 150 partially disposed through the expandable introducer 110. As illustrated, a distal portion of the expandable introducer 110 and the expandable member 120 remains in the unexpanded configuration, and a proximal portion of the expandable introducer 110 and the expandable member 120 is in the expanded configuration. For example, the expander member 160, which has a maximum diameter $D_{160}$ that is greater than an inner diameter of the lumen 117, has caused or induced at least a portion of the expandable member 120 to transition or expand from the unexpanded configuration to the expanded configuration.

FIG. 5C depicts the expander 150 fully disposed through the expandable introducer 110. As illustrated, at least a portion of the expander member 160 extends distally from the distal end 113 of the expandable introducer 110. Furthermore, the expandable introducer 110 and the expandable member 120 have been expanded or transitioned to the expanded configuration. That is, due at least in part to its maximum diameter $D_{160}$, the outer surface of the expander member 160 has applied or exerted a force on the expandable member 120 and/or the inner surface of the expandable introducer 110 such that the expandable introducer 110 and the expandable member 120 have expanded or transitioned from the unexpanded configuration to the expanded configuration. Stated another way, the expandable introducer 110 has expanded from a 5 French configuration to a 7 French configuration. Again, as discussed above, other sizes of the expandable introducer 110 are also within the scope of this disclosure.

Figure 5D:
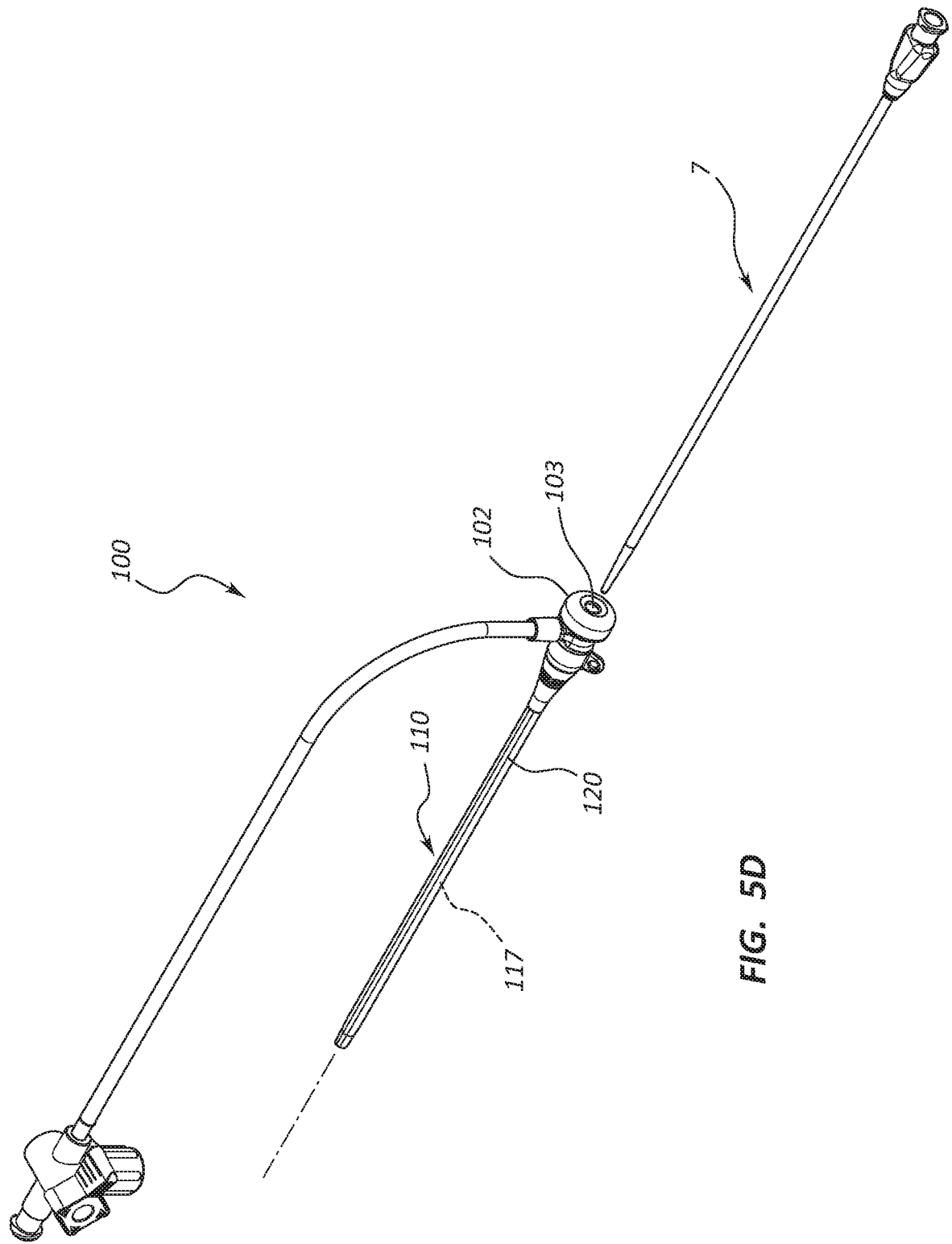
FIG. 5D is a perspective view of the expandable introducer assembly and the expander of FIG. 5A in a fourth configuration.

FIG. 5D depicts the expandable introducer 110 in the expanded configuration (e.g., a 7 French configuration). As illustrated, the expander 150 has been removed or retrieved from within the expandable introducer 110. The expandable introducer 110, which is in the expanded configuration, may be configured to receive a dilator 7. For example, the dilator 7 may be a 7 French dilator, and the dilator 7 may be displaced (e.g., by a practitioner) through the lumen 117 of the expandable introducer 110.

As discussed above in reference to the dilator 5, the opening 103 at the distal end of the hub 102 may be configured to receive the dilator 7. The dilator 7 may then pass through a lumen of the hub 102 and into the lumen 117 of the expandable introducer 110. FIG. 5D depicts the dilator 7 before the dilator 7 has been disposed in the expandable introducer 110 (or after the dilator 7 has been removed from the expandable introducer 110).

The dilator 7 may be more rigid than the expandable introducer 110. For example, the dilator 7 may be formed from a material that is more rigid than the material from which the expandable dilator 110 is formed. A wall of the dilator 7 may also, or alternatively, be thicker than the walls of the expandable introducer 110.

Figure 6A:
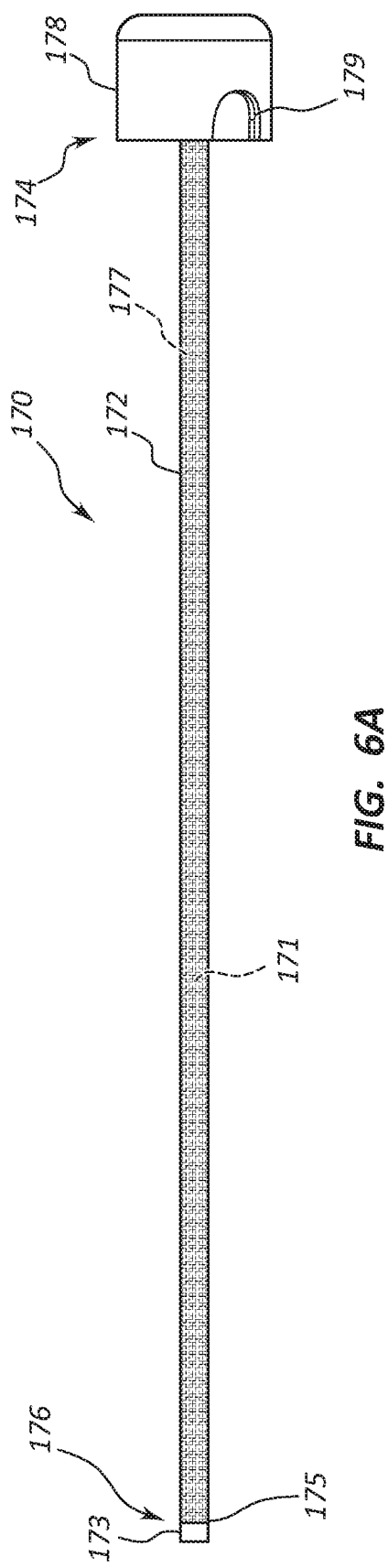
FIG. 6A is a side view of an elongate support member.
Figure 6B:
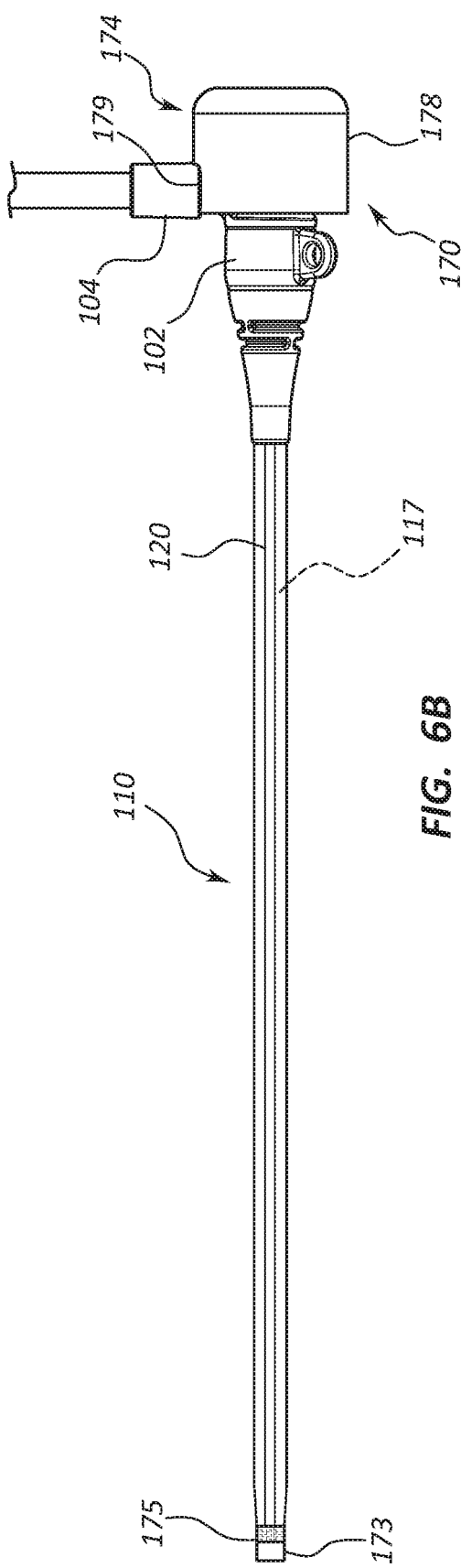
FIG. 6B is a side view of the elongate support member of FIG. 6A and a portion of the expandable introducer assembly of FIG. 1A.

FIG. 6A is a side view of a support member or expanded support member 170. FIG. 6B illustrates the support member 170 upon disposition of the support member 170 within at least a portion of the expandable introducer 110. As depicted, the support member 170 can include an elongate member 172 extending between a proximal end portion 174 and a distal end portion 176, and a distal tip 173 disposed at or coupled to a distal end 175 of the support member 170. The distal tip 173 may be formed from a more flexible, pliable, and/or compressible material than the remaining portions or components of the support member 170 (i.e., the distal tip 173 may be atraumatic). Such a configuration of the distal tip 173 may aid in limiting or preventing damage to the vasculature of a subject, for example, when the support member 170 is in use in the subject.

The support member 170 can further include a lumen 171 disposed within at least a portion of the elongate member 172. Furthermore, the lumen 171 may extend between the proximal end portion 174 and the distal end portion 176 of the support member 170. In certain embodiments, the lumen 171 may extend through only a portion of the length of the support member 170.

In some embodiments, the support member 170 may be configured to be disposed within the lumen 117 of the expandable introducer 110 when the expandable introducer 110 is in the expanded configuration. The support member 170 (when disposed within the lumen 117 of the expandable introducer 110) may reinforce or support the expandable introducer 110 in the expanded configuration. For example, the support member 170 may inhibit or prevent transition of the expandable introducer 110 from the expanded configuration to the unexpanded configuration. Stated another way, the support member 170 may be configured to maintain or substantially maintain the expandable introducer 110 and/or the expandable member 120 in the expanded configuration and reinforce the expandable introducer 110 while in use.

In certain embodiments, a reinforcement member 177 may be disposed within or coupled to at least a portion of the support member 170. For example, the reinforcement member 177 may be disposed within or coupled to at least a portion of the elongate member 172. In various embodiments, the reinforcement member 177 may comprise at least one of a braid, a plurality of braids, a wire, a plurality of wires, or another suitable reinforcing component. In some embodiments, the reinforcement member 177 may formed from one or more of a metal (e.g., nitinol), a polymer (e.g., a rigid polymer), or another suitable material.

The support member 170 can further comprise a cap 178. The cap 178, as illustrated, can be coupled to the proximal end portion 174 of the support member 170. In some embodiments, the cap 178 may be integral with the elongate member 172. In some other embodiments, the cap 178 may be discrete from the elongate member 172. The cap 178 may be shaped such that the cap 178 or at least a portion of the cap 178 is disposable around at least a portion of the hub 102 and/or the sidearm catheter 104.

As depicted, the cap 178 can include a notch 179. In some embodiments, the notch 179 may be shaped such that the notch 179 and/or the cap 178 may be disposed around at least a portion of the hub 102 and/or the sidearm catheter 104. For example, the notch 179 may be U-shaped such that the notch 179 can be disposed around at least a portion of the sidearm catheter 104. In some embodiments, the notch 179 may be square-shaped, semi-circular, or another suitable shape.

In some embodiments, a continuous the support member 170 may tend to block or occlude passage (e.g., of a fluid) from the sidearm catheter 104 to the lumen 171 of the support member 170. Accordingly, in some embodiments a side bore or opening (not shown) may be disposed in the support member 170, wherein the side bore is configured and/or positioned to align with a lumen of the sidearm catheter 104. Such a configuration can provide fluid communication between each of the sidearm catheter 104 and the lumen 171 of the support member 170. The notch 179 may be configured to align the side bore with the lumen of the sidearm catheter 104.

The cap 178 may also include an aperture or opening (not shown) such that an elongate medical device may be displaced through the cap 178 and into the lumen 171 of the support member 170. In various embodiments, the aperture may comprise a seal such that upon displacement of an elongate medical device through the opening, a seal may be formed between the support member 170 and an outside surface of the elongate medical device. In some embodiments, the cap 178 may include a coupling mechanism (not shown), wherein the coupling mechanism is configured to securely couple the support member 170 to the hub 102 (e.g., to limit or prevent separation or unintended separation of the support member 170 from the expandable introducer 110, and vice versa).

Figure 7:
FIG. 7 is a side view of an exchange dilator.

FIG. 7 depicts an exchange dilator 180. The exchange dilator 180, as depicted, includes an elongate member 182 extending between a proximal end portion 184 and a distal end portion 186. The exchange dilator 180 can further comprise a lumen 181 disposed within the elongate member 182 and extending between each of the proximal end portion 184 and the distal end portion 186. In some embodiments, the lumen 181 may extend through only a portion of the exchange dilator 180. The proximal end portion 184 can be tapered. In some embodiments, the taper of the proximal end portion 184 may be about 5° relative to a longitudinal axis of the exchange dilator 180. In some other embodiments, the taper of the proximal end portion 184 may be between about 1° and about 10° relative to a longitudinal axis of the exchange dilator 180, between about 2° and about 9° relative to the longitudinal axis of the exchange dilator 180, between about 3° and about 8° relative to the longitudinal axis of the exchange dilator 180, between about 4° and about 6° relative to the longitudinal axis of the exchange dilator 180, or another suitable degree relative to the longitudinal axis of the exchange dilator 180.

The distal end portion 186 can also be tapered. In certain embodiments, the taper of the distal end portion 186 may be about 5° relative to a longitudinal axis of the exchange dilator 180. In certain other embodiments, the taper of the distal end portion 186 may be between about 1° and about 10° relative to a longitudinal axis of the exchange dilator 180, between about 2° and about 9° relative to the longitudinal axis of the exchange dilator 180, between about 3° and about 8° relative to the longitudinal axis of the exchange dilator 180, between about 4° and about 6° relative to the longitudinal axis of the exchange dilator 180, or another suitable degree relative to the longitudinal axis of the exchange dilator 180. In various embodiments, the taper of the proximal end portion 184 may be substantially symmetrical to the taper of the distal end portion 186. In various other embodiments, the taper of the proximal end portion 184 may be greater than the taper of the distal end portion 186, or vice versa. In yet other various embodiments, the proximal end portion 184 may not be tapered while the distal end portion 186 is tapered, or vice versa.

Also disclosed herein are expandable introducer systems. In some embodiments, the expandable introducer system may include one or more of the following: the expandable introducer assembly 100; the expandable introducer 110; the expander 150, 250; the support member 170; and/or the exchange dilator 180. In certain embodiments, the expandable introducer system may be provided in a kit.

In various embodiments, the expandable introducer 110, the hub 102, the support member 170, the exchange dilator 180, or any other suitable component of the expandable introducer system may be longitudinally openable and/or separable. Stated another way, the expandable introducer 110, the hub 102, the support member 170, and/or the exchange dilator 180 may be splittable, sliceable, and/or tearable to allow or permit the expandable introducer 110, the support member 170, and/or the exchange dilator 180 to be separated into two lengthwise portions, for example, when the expandable introducer 110, the support member 170, and/or the exchange dilator 180 is removed from the subject. Once the expandable introducer 110, the support member 170, and/or the exchange dilator 180 has been separated, the expandable introducer 110, the support member 170, and/or the exchange dilator 180 can be removed from the operating theater. In some other embodiments, the expandable introducer 110, the support member 170, and/or the exchange dilator 180 may not be longitudinally openable or separable.

In some embodiments, one or more markers, such as a radiopaque band, may be disposed on a portion or portions of the expandable introducer, the expander, the support member, and/or the exchange dilator to aid in placement or use thereof (i.e., during a medical procedure).

Methods of expanding an expandable introducer from an unexpanded configuration to an expanded configuration are also disclosed. In some embodiments, the methods of expanding the expandable introducer can comprise disposing an expander within a lumen of the expandable introducer. The expander can then be distally displaced through at least a portion of the lumen. In various embodiments, the expander may include an expander member as described above. Disposition and/or displacement of the expander and the expander member through the lumen of the expandable introducer can exert, or be configured to exert, an outward radial force on an interior surface of the expandable introducer. In certain embodiments, such an outward radial force may expand or transition at least a portion of the expandable introducer from the unexpanded configuration to the expanded configuration. For example, the outward radial force may cause the first, second, and/or third panels of the expandable member to unfold, fan out, or spread apart. The outward radial force may also cause the first and/or second folds of the expandable member to unfold or spread apart.

In some embodiments, the portion of the expandable introducer that expands may be an expandable member that is disposed along a portion of the expandable introducer, such as the expandable member 120 shown in FIGS. 1B and 1C. As described above, the expandable member 120 may comprise an outer panel 127, an inner panel 129, and a medial panel 128 disposed between the outer panel 127 and the inner panel 129. In the unexpanded configuration, the inner panel 129, the medial panel 128, and the outer panel 127 may be each layered against each other. In various embodiments, the methods of expanding the expandable introducer 110 can comprise displacing or spreading the inner panel 129, the medial panel 128, and the outer panel 127 away from each other (i.e., via the expander) to expand the expandable introducer 110 from the unexpanded configuration to the expanded configuration.

In certain embodiments, the methods of expanding the expandable introducer from an unexpanded configuration to an expanded configuration may also include positioning at least a portion of the expandable introducer within a vessel of a subject. As described above, disposing the material from which the expandable introducer is formed at about body temperature can allow the material to soften and become more pliable as the material warms from about room temperature to about body temperature.

The methods of expanding the expandable introducer from an unexpanded configuration to an expanded configuration may further include retrieving the expander from the lumen of the expandable introducer and disposing at least a portion of a support member within the lumen of the expandable introducer. Disposition of the support member within the lumen of the expandable introducer can aid in maintaining the expandable introducer in the expanded configuration. For example, the support member may limit or prevent refolding or reengagement of the first, second, and/or third panels of the expandable member. The support member may also limit or prevent refolding of the first and/or second folds of the expandable member.

Figure 8A:
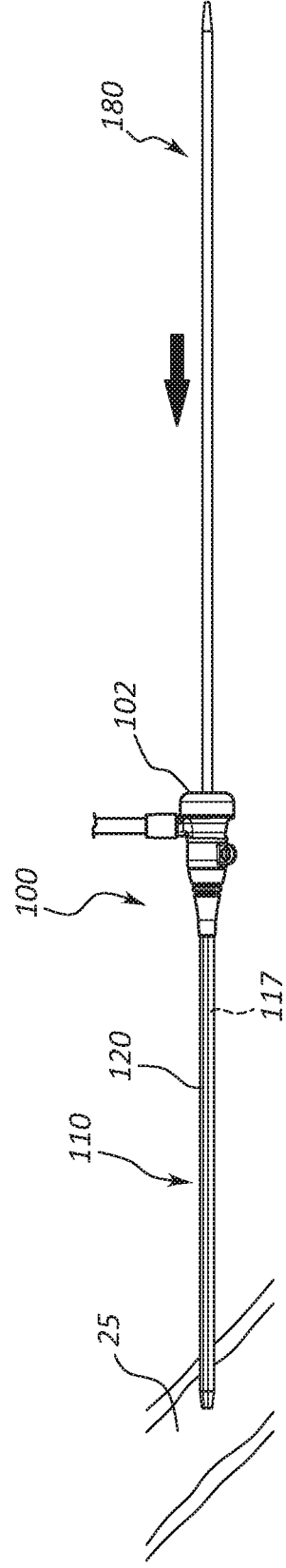
FIG. 8A depicts the disposition of the exchange dilator of FIG. 7 within a portion of the expandable introducer assembly of FIG. 1A.
Figure 8B:
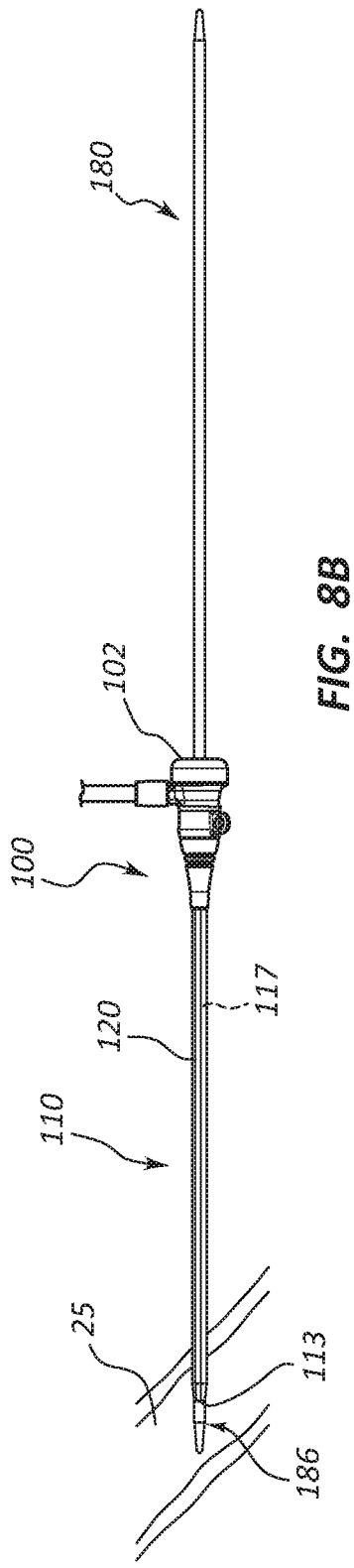
FIG. 8B depicts the disposition of a portion of the exchange dilator of FIG. 8A within a vessel of a subject.

FIGS. 8A-8E depict a method of using the exchange dilator 180 and the expandable introducer 110. FIG. 8A illustrates the expandable introducer assembly 100, wherein the expandable introducer 110 is disposed within a vessel 25 of a subject. As illustrated, the expandable introducer 110 is in the expanded configuration. In some embodiments, the exchange dilator 180 may be displaced through the hub 102 and into the lumen 117 of the expandable introducer 110 as indicated by the arrow. With reference to FIG. 8B, the exchange dilator 180 is disposed within the expandable introducer 110, and the distal end portion 186 of the exchange dilator 180 is disposed distally of the distal end 113 of the expandable member 120.

Figure 8C:
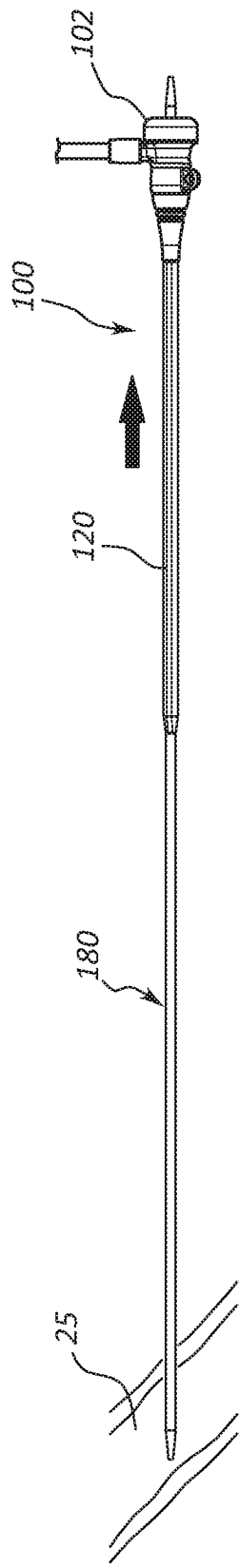
FIG. 8C depicts the removal of the expandable introducer assembly from the exchange dilator of FIG. 8A.
Figure 8D:
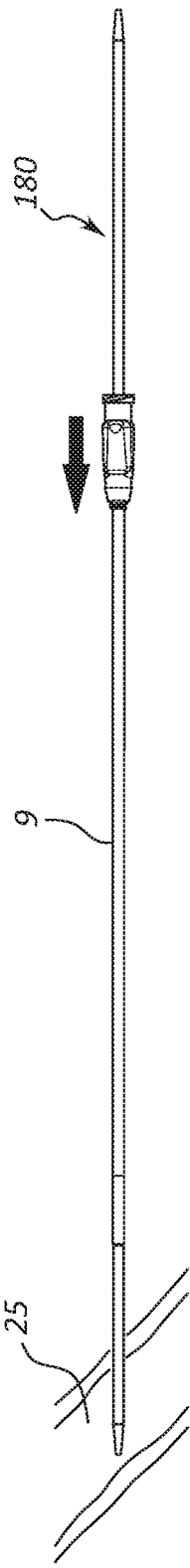
FIG. 8D depicts the disposition of a second larger fixed dilator over a portion of the exchange dilator of FIG. 8A.
Figure 8E:
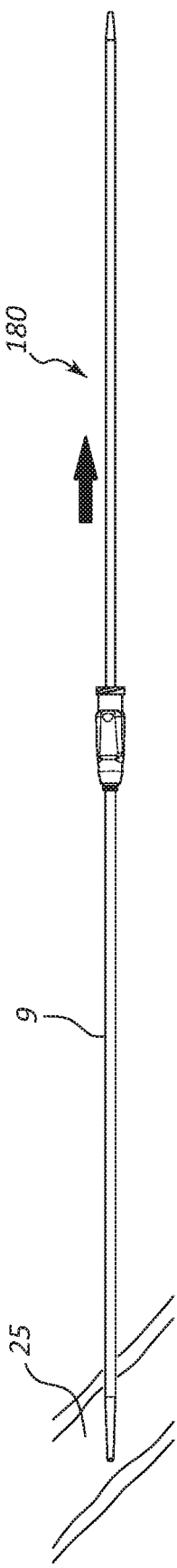
FIG. 8E depicts the removal of the exchange dilator of FIG. 8A from within the second larger fixed dilator of FIG. 8D and the vessel of the subject.

As illustrated in FIG. 8C, in some embodiments, the expandable introducer assembly 100 may be removed or retrieved from the vessel 25 and/or from around the exchange dilator 180 as depicted by the arrow. Once the expandable introducer assembly 100 has been removed from around the exchange dilator 180, a second larger fixed dilator or other suitable elongate medical device 9 may be disposed over the exchange dilator 180 and into the vessel 25 as indicated by the arrow (see FIG. 8D). In various embodiments, once at least a portion of the second larger fixed dilator 9 is disposed within the vessel 25, the exchange dilator 180 may be removed or retrieved from within the vessel 25 and/or the second larger fixed dilator 9 as indicated by the arrow in FIG. 8E. Upon removal of the exchange dilator 180, the second larger fixed dilator 9 may be used for a medical procedure.

As can be appreciated, additional methods and/or method steps can be derived from FIGS. 1A-8E and the corresponding disclosure. Any methods disclosed herein include one or more steps or actions for performing the described method.

The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A method of expanding an expandable introducer from an unexpanded configuration to an expanded configuration, the method comprising:
   simultaneously disposing an expander and a support member within a lumen of the expandable introducer;
   distally displacing the expander and the support member through the lumen such that an expander member of the expander exerts an outward radial force on an interior surface of the expandable introducer and such that a portion of the expandable introducer expands from the unexpanded configuration to the expanded configuration; and
   retrieving the expander from the lumen of the expandable introducer without withdrawing the support member, such that the support member remains in an expanded state within the lumen of the expandable introducer to maintain the expandable introducer in the expanded configuration while the expandable introducer is in use.

2. The method of claim 1, wherein the portion of the expandable introducer that expands is an expandable member disposed along a portion of the expandable introducer, wherein the expandable member comprises an outer panel, an inner panel, and a medial panel disposed between the outer panel and the inner panel, and wherein the inner panel, the medial panel, and the outer panel are each layered against each other in the unexpanded configuration.

3. The method of claim 2, further comprising:
displacing the inner panel, the medial panel, and the outer panel away from each other to expand the expandable introducer from the unexpanded configuration to the expanded configuration.

4. The method of claim 3, wherein the outer panel, the inner panel, and the medial panel of the expandable member are integral and folded relative to each other.

5. The method of claim 4, wherein in displacing the inner panel, the medial panel, and the outer panel unfold relative to each other to expand the expandable introducer to the unexpanded configuration.

6. The method of claim 2, wherein a thickness of the outer and inner panels is greater than a thickness of the medial panel.

7. The method of claim 6, wherein the expandable introducer further comprises an elongate member, the elongate member comprises a first wall that extends circumferentially from a first end to a second end, and wherein the expander member is disposed between the first end and the second end.

8. The method of claim 7, wherein the inner panel of the expandable member extends from the first end of the first wall and the outer panel of the expandable member extends from the second end of the first wall.

9. The method of claim 7, wherein a thickness of the expandable member in the unexpanded configuration is equivalent to a thickness of the first wall.

10. The method of claim 1, further comprising:
positioning a portion of the expandable introducer within a vessel of a subject;
allowing the portion of the expandable introducer positioned within the vessel to come to a body temperature of the subject prior to distally displacing the expander through the lumen of the expandable introducer.

11. The method of claim 1, wherein the expander member is disposed around at least a portion of an outer surface of the expander.

12. The method of claim 1, wherein the expander member is disposed at a distal end of the expander.

13. The method of claim 1, wherein the expander member comprises a balloon.

14. The method of claim 1, further comprising expanding the expander member to an expanded configuration to expand the expandable introducer from the unexpanded configuration to the expanded configuration.

15. The method of claim 14, further comprising relaxing the expander member to a relax configuration.

16. The method of claim 15, wherein the expander is retrieved from the lumen of the expandable introducer after the expander member is in the relaxed configuration.

17. The method of claim 1, wherein the expandable introducer transitions from a 5 French configuration to a 7 French configuration.

18. The method of claim 1, wherein the support member comprises an elongate member including a distal end and a proximal end and a reinforcement member that is disposed within a portion of the elongate member of the support member.

19. The method of claim 18, wherein the reinforcement member comprises at least one of a braid and a wire.

* * * * *